US012802810B2

(12) United States Patent
Schmidt et al.

(10) Patent No.: US 12,802,810 B2
(45) Date of Patent: Nov. 17, 2026

(54) REMOTE ASSISTANCE AVAILABILITY COMMUNICATION SYSTEM

(71) Applicant: KONINKLIJKE PHILIPS N.V., Eindhoven (NL)

(72) Inventors: Joachim Dieter Schmidt, Hamburg (DE); Thomas Erik Amthor, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 609 days.

(21) Appl. No.: 17/093,685

(22) Filed: Nov. 10, 2020

(65) Prior Publication Data

US 2021/0142895 A1 May 13, 2021

Related U.S. Application Data

(60) Provisional application No. 62/934,017, filed on Nov. 12, 2019.

(51) Int. Cl.
*G16H 40/67* (2018.01)
*G06Q 10/0631* (2023.01)
*G16H 40/40* (2018.01)

(52) U.S. Cl.
CPC ............. *G16H 40/67* (2018.01); *G16H 40/40* (2018.01); *G06Q 10/063116* (2013.01)

(58) Field of Classification Search
CPC .. G06Q 20/18; G06Q 20/322; G06Q 30/0278; G06Q 30/0631; G06Q 10/30;
(Continued)

(56) References Cited

U.S. PATENT DOCUMENTS 8,170,887 B2 5/2012 Rosenfeld
2007/0206086 A1 * 9/2007 Baron .................... H04N 7/147 348/E7.081

(Continued)

FOREIGN PATENT DOCUMENTS

AU 2014101286 A4 * 11/2014 ........... G06F 19/323

OTHER PUBLICATIONS

Cohen GI. "A practical guide to graphic communication for quality assurance, education, and patient care in echocardiography." Echocardiography. Sep. 2019; 36(9):1747-1754. doi: 10.1111/echo.14464. Epub Sep. 21, 2019. PMID: 31541574; PMCID: PMC6856834.) (Year: 2019).*

*Primary Examiner* — Rachel L. Porter

(57) ABSTRACT

An apparatus provides assistance by a remote operator to a local operator of a medical imaging device (2) disposed in a medical imaging device bay (3) via a communication link (14) from a remote service center (4) to the medical imaging device bay. The apparatus includes a workstation (12) disposed in the remote service center including at least one workstation display (24). At least one electronic processor (20, 20') is programmed to: mirror a display (24') of an imaging device controller (10) of the medical imaging device at the at least one workstation display; present video (17), on the at least one workstation display, of the medical imaging device acquired by a camera (16) disposed in the medical imaging device bay; generate a timeline (30) of a schedule (108) of the remote operator, wherein the generated timeline includes a plurality of time slots (34) and an engagement status (36) of the remote operator for each time slot; and control a display device (24') in the medical imaging device bay to display the generated timeline.

20 Claims, 4 Drawing Sheets

(58) Field of Classification Search

CPC .... G06Q 30/0283; G06Q 10/02; G06Q 10/10; G06Q 30/0237; G06Q 10/083; G06Q 20/208; G06Q 30/0601; G06Q 30/0643; G06Q 20/10; G06Q 50/10; G06Q 30/02; G06Q 30/0621; G06Q 10/0838; G06Q 20/40145; G06Q 30/00; G06Q 10/00; G06Q 10/1095; G06Q 20/203; G06Q 50/26; G06Q 30/0208; G06Q 30/0279; G06Q 30/06; G06Q 40/08; G06Q 10/0833; G06Q 30/0201; G06Q 50/00; G06Q 20/042; G06Q 20/206; G06Q 20/209; G06Q 20/34; G06Q 30/018; G06Q 30/0282; G06Q 30/08; G06Q 50/205; G06Q 50/50; G06Q 10/06316; G06Q 10/20; G06Q 20/04; G06Q 20/123; G06Q 20/202; G06Q 20/4016; G06Q 30/012; G06Q 30/0185; G06Q 30/0206; G06Q 30/0269; G06Q 50/22; G06Q 10/087; G06Q 10/107; G06Q 20/20; G06Q 20/204; G06Q 20/22; G06Q 30/016; G06Q 30/0241; G06Q 30/0609; G06Q 30/0623; G06Q 30/0641; G06Q 99/00; G06Q 20/00; G06Q 20/02; G06Q 20/085; G06Q 20/102; G06Q 20/108; G06Q 20/1085; G06Q 20/207; G06Q 20/326; G06Q 20/3274; G06Q 20/381; G06Q 20/4014; G06Q 20/405; G06Q 30/0207; G06Q 30/0611; G06Q 30/0633; G06Q 30/0639; G06Q 40/02; G06Q 40/04; G06Q 40/123; G06Q 10/063118; G06Q 10/06; G06Q 10/063116; G06Q 10/06313; G06Q 10/06314; G06Q 10/06315; G06Q 10/109; G06Q 10/1097; G06Q 10/063114; G06Q 50/02; G06Q 10/06312; G06Q 50/16; G06Q 50/30; H04L 67/535; H04L 67/52; H04L 51/224; H04L 67/04; H04L 67/60

See application file for complete search history.

(56) References Cited

U.S. PATENT DOCUMENTS

| | | | | |
|---|---|---|---|---|
| 2008/0204357 | A1* | 8/2008 | Azulai | H04L 65/613<br>345/2.2 |
| 2011/0157480 | A1* | 6/2011 | Curl | G16H 40/67<br>348/739 |
| 2015/0035959 | A1* | 2/2015 | Amble | A61B 5/0077<br>348/74 |
| 2015/0286788 | A1* | 10/2015 | Arkoff | G16H 40/20<br>705/2 |
| 2016/0300024 | A1 | 10/2016 | Janssen | |
| 2017/0105701 | A1* | 4/2017 | Pelissier | A61B 8/461 |
| 2017/0221013 | A1* | 8/2017 | Weksler | H04W 4/027 |
| 2017/0262602 | A1* | 9/2017 | Schweizer | G05B 19/124 |
| 2019/0236499 | A1* | 8/2019 | Reyes | G16H 40/20 |
| 2020/0210964 | A1* | 7/2020 | Monovich | G01C 21/343 |
| 2021/0093285 | A1* | 4/2021 | Hader | G16H 80/00 |

* cited by examiner

REMOTE ASSISTANCE AVAILABILITY COMMUNICATION SYSTEM

CROSS REFERENCE TO RELATED APPLICATIONS

This application claims the benefit of U.S. Provisional Patent Application No. 62/934,017 filed Nov. 12, 2019. This application is hereby incorporated by reference herein.

FIELD

The following relates generally to the imaging arts, remote imaging assistance arts, remote imaging examination monitoring arts, and related arts.

BACKGROUND

Medical imaging, such as computed tomography (CT) imaging, magnetic resonance imaging (MRI), positron emission tomography (PET) imaging, fluoroscopy imaging, and so forth, is a critical component of providing medical care, and is used in a wide range of medical fields, such as cardiology, oncology, neurology, orthopedics, to name a few. The operator of the medical imaging device used to acquire the medical images is typically a trained technician, while interpretation of the medical images is often handled by the patient's general practitioner (GP) physician or a medical specialist such as a radiologist, cardiologist, oncologist, orthopedic surgeon, or so forth.

The operator of a medical imaging device of a given modality (CT, MRI, PET, etc.) is often expected to be qualified to perform a wide range of different imaging procedures in service to GP physicians, cardiologists, oncologists, or so forth. For example, a cardiac imaging procedure may be very different from an imaging procedure targeting a known or suspected oncological tumor, which may be very different again from an orthopedic imaging procedure, etc. This requires the imaging device operator to be highly qualified, and preferably experienced, in a diverse range of different types of imaging procedures. Furthermore, the increased demand for medical imaging services has led to most hospitals providing medical imaging departments, and additional independent imaging laboratories that provide services on a contractual basis. This has led strong demand for highly qualified and experienced medical imaging device operators.

The problem of getting highly qualified operators for complex imaging examinations for each imaging site has driven the concept of providing assistive medical expertise via remote service centers. These provide virtual availability of senior technologists, sometimes referred to as a remote operator, in case an on-site operator lacks the required skills for a scheduled examination or runs into unexpected difficulties. In such cases, the remote operator would remotely assist the on-site operator by receiving real-time views of the situation in terms of screen mirroring of the imaging device controller display and video of the imaging bay.

Existing remote service centers provide for remote operator assistance in performing medical imaging. In existing setups, the remote operator is assigned certain imaging examination bays and is provided with the examination schedules for their assigned bays. The remote operator can observe the local operator/patient interactions via a video camera, and also sees a mirror of the imaging device controller at a remote operator computer. Assistance may be initiated by the remote operator based on recognized difficulty of an imaging examination, or may be initiated by the local operator if, for example, a problem is encountered during an imaging examination. The provided assistance is typically telephonic.

The following discloses certain improvements to overcome these problems and others.

SUMMARY

In one aspect, an apparatus provides assistance by a remote operator to a local operator of a medical imaging device disposed in a medical imaging device bay via a communication link from a remote service center to the medical imaging device bay. The apparatus includes a workstation disposed in the remote service center including at least one workstation display. At least one electronic processor is programmed to: mirror a display of an imaging device controller of the medical imaging device at the at least one workstation display; present video, on the at least one workstation display, of the medical imaging device acquired by a camera disposed in the medical imaging device bay; generate a timeline of a schedule of the remote operator, wherein the generated timeline includes a plurality of time slots and an engagement status of the remote operator for each time slot; and control a display device in the medical imaging device bay to display the generated timeline.

In another aspect, a non-transitory computer readable medium stores instructions executable by at least one electronic processor to perform a method of providing assistance by a remote operator to a local operator of a medical imaging device disposed in a medical imaging device bay via a communication link from a remote service center to the medical imaging device bay. The method includes: mirroring a display of an imaging device controller of the medical imaging device at a workstation disposed in the remote service center including at least one workstation display; presenting, on the at least one workstation display, video of the medical imaging device acquired by a camera disposed in the medical imaging device bay; generating a timeline of a schedule of the remote operator in which the generated timeline includes a plurality of time slots and an engagement status of the remote operator for each time slot; and controlling a display device in the medical imaging device bay to display the generated timeline. The method provides assistance by the remote operator to a plurality of local operators including said local operator. Each local operator is a local operator of a respective medical imaging device disposed in a respective medical imaging device bay. The controlling of the display device in the medical imaging device bay to display the generated timeline includes controlling display devices in the respective medical imaging device bays to display the generated timeline on each respective display device.

In another aspect, a method of providing assistance by a remote operator to a local operator of a medical imaging device disposed in a medical imaging device bay via a communication link from a remote service center to the medical imaging device bay includes: mirroring a display of an imaging device controller of the medical imaging device at a workstation disposed in the remote service center including at least one workstation display; presenting, on the at least one workstation display, video of the medical imaging device acquired by a camera disposed in the medical imaging device bay; generating a timeline of a schedule of the remote operator, wherein the generated timeline includes a plurality of time slots and an engagement status of the remote operator for each time slot; at a display device in the medical imaging bay, displaying to display the generated timeline; receiving at least one request from a local operator at the medical imaging device bay, the at least one request indicating a need for assistance at a requested time; and updating the timeline based on the requested time of the at least one request.

One advantage resides in allowing remote operators to provide a schedule to one or more local operators at different facilities.

Another advantage resides in allowing local operators to adjust their schedule based on an availability of a remote operator.

Another advantage resides in allowing local operators to send messages to a remote operator requesting assistance.

Another advantage resides in generating and updating a schedule of the remote operator to local operators.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
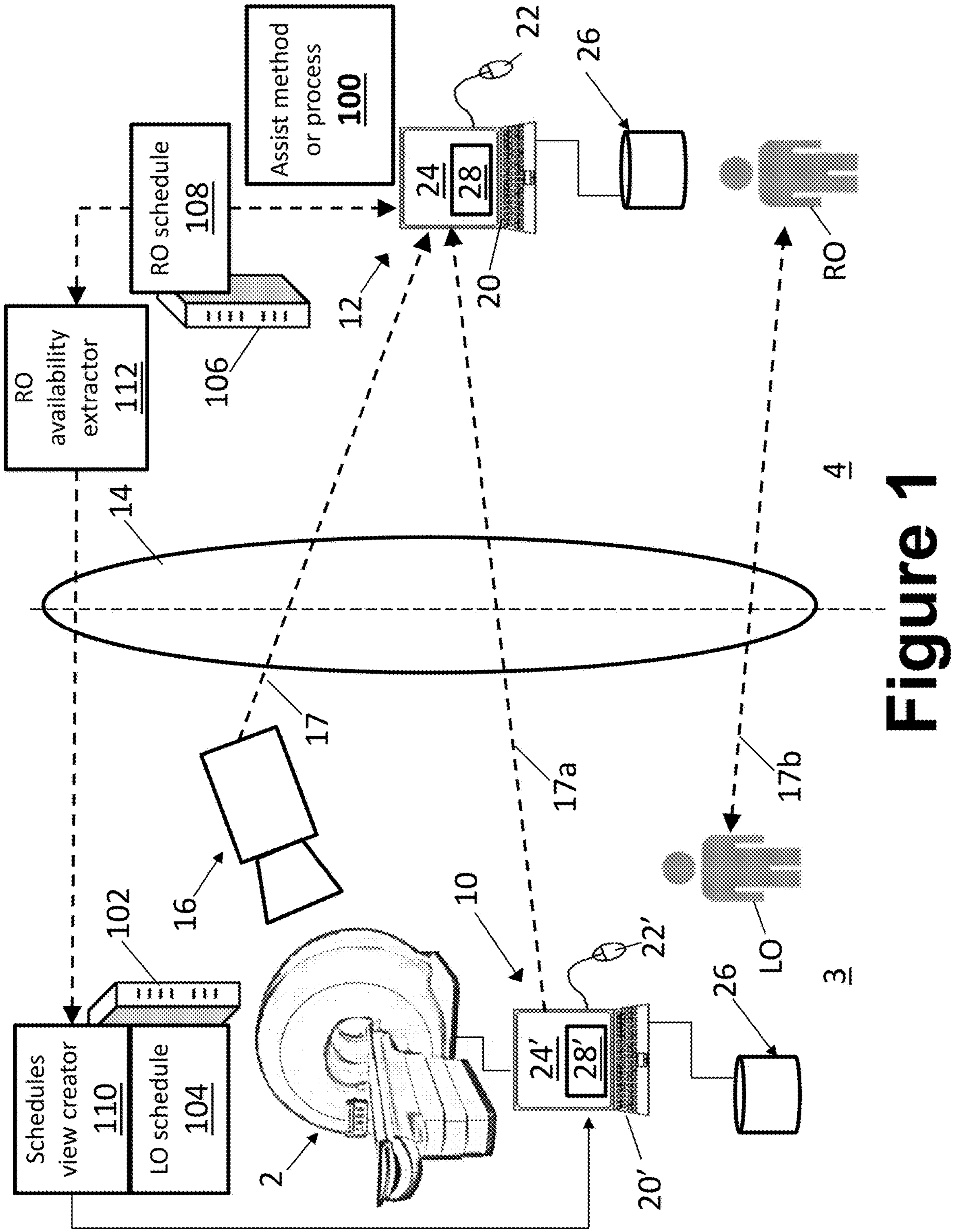
FIG. 1 diagrammatically illustrates an illustrative apparatus for providing remote assistance in accordance with the present disclosure.

As recognized herein, a problem exists in that the local operator is unaware of the schedule and current availability of the remote operator. Hence, if the local operator requests assistance but the remote operator is busy assisting another bay, then the imaging procedure is delayed until the remote operator becomes available. By contrast, if the local operator knows the remote operator is currently unavailable, then the local operator can take various actions to improve workflow efficiency, such as performing an easier scheduled imaging examination first, performing less challenging imaging sequences in the easier examination, or so forth.

In some embodiments disclosed herein, to provide the local operator with information about the remote operator's status, the disclosed system transfers the remote operator's schedule to the local operator. However, to avoid patient privacy issues or possible improper transfer of client information (for example, if the remote operator is servicing multiple client medical institutions), the transferred remote operator's schedule is simplified to merely designating time blocks as "busy" or "free", or providing limited information on the "busy" blocks such as the type of imaging procedure with which the remote operator is scheduled to assist. Optionally, for those remote operator time blocks in which the remote operator is scheduled to assist the local operator (or, in a variant approach, a bay at the local operator's hospital) more information may be provided in the transferred remote operator's schedule Furthermore, the system transfers real-time updates of the remote operator's schedule to the local operator's system. Optionally, the system may also transfer the real-time state of the local operator's schedule to the remote scheduling system. This permits the remote scheduler to adjust the remote operator's schedule based on delays at the local hospital as recorded in the local operator's schedule. Conversely, optionally the local operator's schedule may be adjusted based on workload of the remote operator, for example by time shifting a scheduled examination with which the local operator will require assistance to a time slot in which the remote operator is available to provide assistance.

In other embodiments disclosed herein, a GUI dialog is provided at the remote operator terminal via which the remote operator can set his or her current status, e.g. "Working schedule based" or "Engaged otherwise" (e.g., handling an unscheduled call for assistance from another local operator). This setting is reported at the local operator's computer, so that the local operator knows the availability of the remote operator.

In some embodiments disclosed herein, the local operator is provided with an assistance request GUI for requesting remote assistance. This GUI preferably allows the local operator to specify a time at which assistance will be needed (e.g., "Need assistance in 10 min" or "Need assistance after contrast agent injected") and/or information on the type of assistance being requested (e.g., "Need assistance in performing contrast agent injection"). The remote operator scheduler then schedules this requested assistance into the remote operator schedule if there are no conflicts at the requested time. (Since the local operator sees the remote operator's schedule, the local operator can attempt to request assistance at an open time slot of the remote operator schedule). If there is a conflict, then the requested assistance is shown on the remote operator's schedule, but is not actually inserted into the schedule. Optionally, if there is a conflict then the system may report back to the local operator an estimated time (or possibly estimated time range) when the remote operator will become available, based on the current remote operator schedule. A similar GUI may be provided to the remote operator so that the remote operator can indicate a time interval of unscheduled unavailability (e.g., "Will not be available for the next 15 minutes.").

In other embodiments disclosed herein, if there are multiple remote operators on staff at the same time, then the system can merge schedules where possible. For example, the local operator may request the assistance of a specific remote operator, or may request assistance without specifying any particular remote operator. In the latter case, the system will send the request to a remote operator who is open at the time of the request. In the former case, if the requested specific remote operator is busy then the system may propose that another remote operator (who is open) handle the request.

With reference to FIG. 1, an apparatus for providing assistance from a remote operator RO to a local operator LO is shown. As shown in FIG. 1, the local operator LO, who operates a medical imaging device (also referred to as an image acquisition device, imaging device, and so forth) 2, is located in a medical imaging device bay 3, and the remote operator RO is disposed in a remote service center 4. The image acquisition device 2 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 2 may also be a hybrid imaging device such as a PET/CT or SPECT/CT imaging system. While a single image acquisition device 2 is shown by way of illustration in FIG. 1, more typically a medical imaging laboratory will have multiple image acquisition devices, which may be of the same and/or different imaging modalities. For example, if a hospital performs many CT imaging examinations and relatively fewer MRI examinations and still fewer PET examinations, then the hospital's imaging laboratory (sometimes called the "radiology lab" or some other similar nomenclature) may have three CT scanners, two MRI scanners, and only a single PET scanner. This is merely an example. Moreover, the remote service center may provide service to multiple hospitals. The local operator controls the medical imaging device 2 via an imaging device controller 10. The remote operator is stationed at a remote workstation 12 (or, more generally, an electronic controller 12). The remote service center 4 may be in the same building as the medical imaging device bay 3, but more typically the remote service center 4 and the medical imaging device bay 3 are in different buildings, and indeed may be located in different cities, different countries, and/or different continents.

As used herein, the term "medical imaging device bay" (and variants thereof) refer to a room containing the medical imaging device 2 and also any adjacent control room containing the medical imaging device controller 10 for controlling the medical imaging device. For example, in reference to an MRI device, the medical imaging device bay 3 can include the radio-frequency (RF) shielded room containing the MRI device 2, as well as an adjacent control room housing the medical imaging device controller 10, as understood in the art of MRI devices and procedures. On the other hand, for other imaging modalities such as CT, the imaging device controller 10 may be located in the same room as the imaging device 2, so that there is no adjacent control room and the medical bay 3 is only the room containing the medical imaging device 2. In addition, while FIG. 1 shows a single medical imaging device bay 3, it will be appreciated that the remote service center 4 (and more particularly the remote workstation 12) is in communication with multiple medical bays via a communication link 14, which typically comprises the Internet augmented by local area networks at the remote operator RO and local operator LO ends for electronic data communications.

As diagrammatically shown in FIG. 1, a camera 16 (e.g., a video camera) is arranged to acquire a video stream 17 of a portion of the medical imaging device bay 3 that includes at least the area of the imaging device 2 where the local operator LO interacts with the patient, and optionally may further include the imaging device controller 10. The video stream 17 is sent to the remote workstation 12 via the communication link 14, e.g. as a streaming video feed received via a secure Internet link. Additionally, a screen mirroring data stream 17*a* is sent from the imaging device controller 10 to the remote workstation 12. The communication link 14 also provides a natural language communication pathway 17*b* for verbal and/or textual communication between the local operator and the remote operator. For example, the natural language communication link 17*b* may be a Voice-Over-Internet-Protocol (VOIP) telephonic connection, an online video chat link, a computerized instant messaging service, or so forth. Alternatively, the natural language communication pathway 17*b* may be provided by a dedicated communication link that is separate from the communication link 14 providing the data communications 17, 17*a*, e.g. the natural language communication pathway 17*b* may be provided via a landline telephone.

FIG. 1 also shows, in the remote service center 4 including the remote workstation 12, such as an electronic processing device, a workstation computer, or more generally a computer, which is operatively connected to receive and present the video 17 of the medical imaging device bay 3 from the camera 16 and to present the screen mirroring data stream 17*a* as a mirrored screen. Additionally or alternatively, the remote workstation 12 can be embodied as a server computer or a plurality of server computers, e.g. interconnected to form a server cluster, cloud computing resource, or so forth. The workstation 12 includes typical components, such as an electronic processor 20 (e.g., a microprocessor), at least one user input device (e.g., a mouse, a keyboard, a trackball, and/or the like) 22, and at least one display device 24 (e.g. an LCD display, plasma display, cathode ray tube display, and/or so forth). In some embodiments, the display device 24 can be a separate component from the workstation 12. The display device 24 may also comprise two or more display devices, e.g. one display presenting the video 17 and the other display presenting the shared screen of the imaging device controller 10 generated from the screen mirroring data stream 17*a*. Alternatively, the video and the shared screen may be presented on a single display in respective windows. The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the remote operator display device 24.

The medical imaging device controller 10 in the medical imaging device bay 3 also includes similar components as the remote workstation 12 disposed in the remote service center 4. Except as otherwise indicated herein, features of the medical imaging device controller 10 disposed in the medical imaging device bay 3 similar to those of the remote workstation 12 disposed in the remote service center 4 have a common reference number followed by a "prime" symbol, and the description of the components of the medical imaging device controller 10 will not be repeated. In particular, the medical imaging device controller 10 is configured to display a GUI 28' on a display device 24' that presents information pertaining to the control of the medical imaging device 2, such as configuration displays for adjusting configuration settings of the imaging device 2, imaging acquisition monitoring information, presentation of acquired medical images, and so forth. It will be appreciated that the screen mirroring data stream 17*a* carries the content presented on the display device 24' of the medical imaging device controller 10.

The remote workstation 12 is configured as described above to perform a method or process 100 for providing assistance the local operator LO. The non-transitory storage medium 26 stores instructions which are readable and executable by the at least one electronic processor 20 of the workstation 12 to perform disclosed operations including performing the method or process 100. In some examples, the method 100 may be performed at least in part by cloud processing. In particular, the GUI 28 presented on the display 24 of the remote workstation 12 preferably includes a window presenting the video 17, and a window presenting the mirrored screen of the medical imaging device controller 10 constructed from the screen mirroring data stream 17*a*. This allows the remote operator RO to be aware of the content of the display of the medical imaging device controller 10 (via the shared screen) and also to be aware of the physical situation, e.g. position of the patient in the medical imaging device 2 (via the video 17). During an imaging procedure, the natural language communication pathway 17*b* is suitably used to allow the local operator LO and the remote operator RO to discuss the procedure and in particular to allow the remote operator to provide advice to the local operator.

With continuing reference to FIG. 1, a server computer 102 maintains a local operator schedule 104 for the medical imaging device bay 3. For example, the server computer 104 may be a hospital-wide server (or server cluster, or cloud computing resource, or so forth) that forms the information technology (IT) infrastructure of the hospital and provides a scheduling system for scheduling medical imaging examinations to be performed by the radiology laboratory of which the medical imaging device bay 3 is a part, and the scheduling system then maintains the local operator schedule 104. Alternatively, the local operator schedule 104 may be maintained by a scheduling system specific to the radiology laboratory, or some other IT architecture may be employed. In similar fashion, a server computer 106 maintains a remote operator schedule 108 for the remote service center 4. While separate local and remote servers 102, 106 are illustrated, in a variant embodiment it is contemplated for a single server computer (or server cluster, or cloud computing resource, or so forth) to maintain both the local operator schedule 104 and the remote operator schedule 108. Other hardware implementations are contemplated; for example, the local operator schedule 104 may be maintained directly by the imaging device controller 10, and/or the remote operator schedule 108 may be maintained by the remote workstation 12.

As disclosed herein, a schedules view creator 110 running on the server computer 102 (as shown) and/or on the medical imaging device controller 10, or on some other computer (not shown) provides the local operator LO with detailed information about both the local operator schedule 104, and also provides less detailed information about the remote operator schedule 108. The latter, less detailed, information is sufficient to inform the local operator LO about current and/or scheduled availability of the remote operator RO, but preferably does not include detailed information that might affect patient privacy or client confidentiality of other clients that may (optionally) be serviced by the remote service center 4. To this end, the remote operator schedule 108 is processed by a local operator availability extractor 112 which extracts remote operator availability information from the remote operator (RO) schedule 108 and conveys the remote operator availability information to the schedules view creator 110 via the communication link 14. The schedules view creator 110 then constructs a display showing the local operator schedule 104 and the remote operator RO availability information, preferably as a graphically represented timeline or other intuitive GUI display which suitably forms content of the GUI 28' shown on the medical imaging device controller 10 and/or on some other computer, and/or on a mobile device (e.g. cellphone or tablet computer), and/or on other electronic device having a display that is also disposed in the imaging device bay 3.

Figure 2:
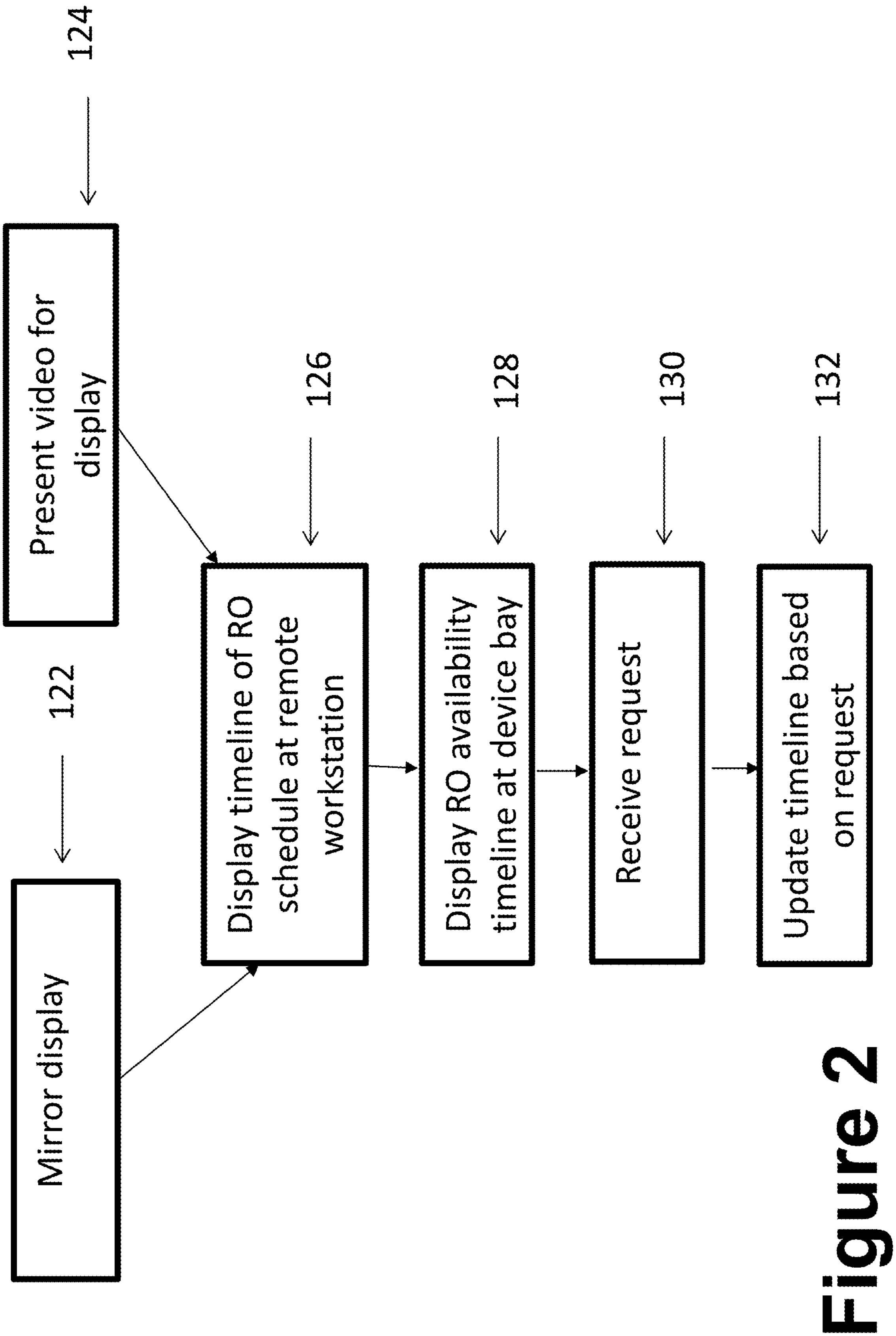
FIG. 2 shows example flow chart operations performed by the apparatus of FIG. 1.

With reference to FIG. 2, and with continuing reference to FIG. 1, an illustrative embodiment of the method 100 and processes performed by the RO availability extractor 112 and the schedules view creator 110 is diagrammatically shown as a flowchart. At an operation 122, the at least one electronic processor 20 of the workstation 12 is programmed to mirror the display 24' of the imaging device controller 10 on the display device 24 of the remote workstation 12 using the screen mirroring data stream 17*a* sent from the imaging device controller 10 to the remote workstation 12. Any commercial or custom-built screen mirroring software can be used for the operation 122.

At an operation 124 performed concurrently with the operation 122, the at least one electronic processor 20 is programmed to present the video 17 of the medical imaging device 2 on the display device 24. To do so, the at least one electronic processor 20 is programmed to present the video stream 17 captured by the camera 16 and present this video stream on the display device 24. The operations 122, 124 correspond to processing performed in accord with the method 100. These operations 122, 124 are typically performed only at times when the remote operator RO is assisting the local operator LO. (At other times, analogous operations may be performed to provide video and screen sharing for some other local operator LO then being assisted by the remote operator RO; or, no video or screen sharing may be running when the remote operator is on break).

Figure 3:
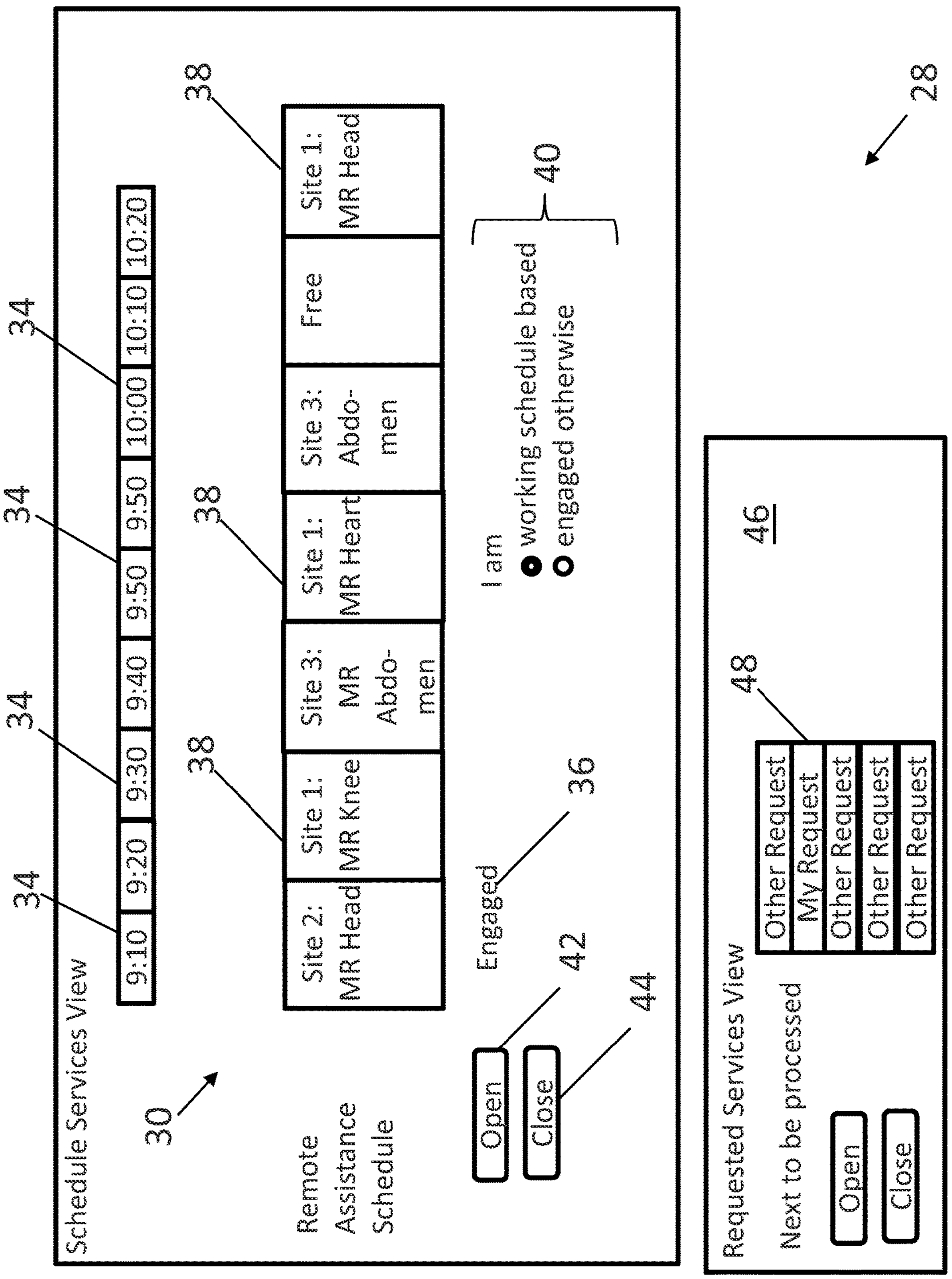
FIGS. 3 and 4 show examples of graphical user interfaces (GUIs) generated by the apparatus of FIG. 1.

With continuing reference to FIGS. 1 and 2, and now with reference to FIG. 3, at an operation 126, the at least one electronic processor 20 is programmed to generate a timeline 30 of the RO schedule 108 of the remote operator RO. The timeline 30 is implemented on the GUI 28 on the display device 24, and is generated by the server 106 and/or the remote workstation 12 from the RO schedule 108.

As shown in FIG. 3, the generated timeline 30 includes a plurality of time slots 34 and an engagement status 36 (e.g., whether the remote operator RO is busy or available) of the remote operator for each time slot. The engagement status 36 in each time slot 34 can include textual information 38 related to a type of work order to be performed in that time slot. For example, the first time slot 34 (e.g., from 9:10-9:20) includes textual information 38 indicating that the work order is an MR imaging session of a head of a patient a medical bay indicated at "Site 2". In another example, the second time slot 34 includes textual information 38 indicating that the work order is an MR imaging session of a knee of a patient a medical bay indicated at "Site 1". In addition, other information other than the textual information 38 can be shown (e.g., pictures, symbols, and so forth). In yet another example, the time slot 34 does not have to include textual information 38. FIG. 3 shows an example of a "free" time slot 34 at 10:10.

In some embodiments, the engagement status 36 of the remote operator RO can be indicated in a variety of manners. In one example, the term "engaged" (or variants thereof) can be displayed on the timeline 30 under the corresponding time slot 34 for the work order on which the remote operator RO is currently assisting or otherwise working on. In another example, the "engaged" time slot 34 of the remote operator RO being "busy" or "engaged" can be indicated by color coding, shading, hatching, etc. that is different from the other time slots.

FIG. 3 also shows that the timeline 30 includes a user dialog 40 in which the remote operator RO can indicate (e.g., with a user input via the at least one user input device 22) whether the remote operator is "working scheduled-based" (i.e., the remote operator is working according to the schedule in the timeline) or is "otherwise engaged" (i.e., the remote operator is not working according to the schedule in the timeline). The timeline 30 can also include an "open" button 42 and a "close" button 44 for the remote operator RO to open or close the timeline 30 as implemented on the GUI 28. The timeline 30 further includes a "requested services view" field 46 that lists one or more requests 48 of one or more local operators LO.

Figure 4:
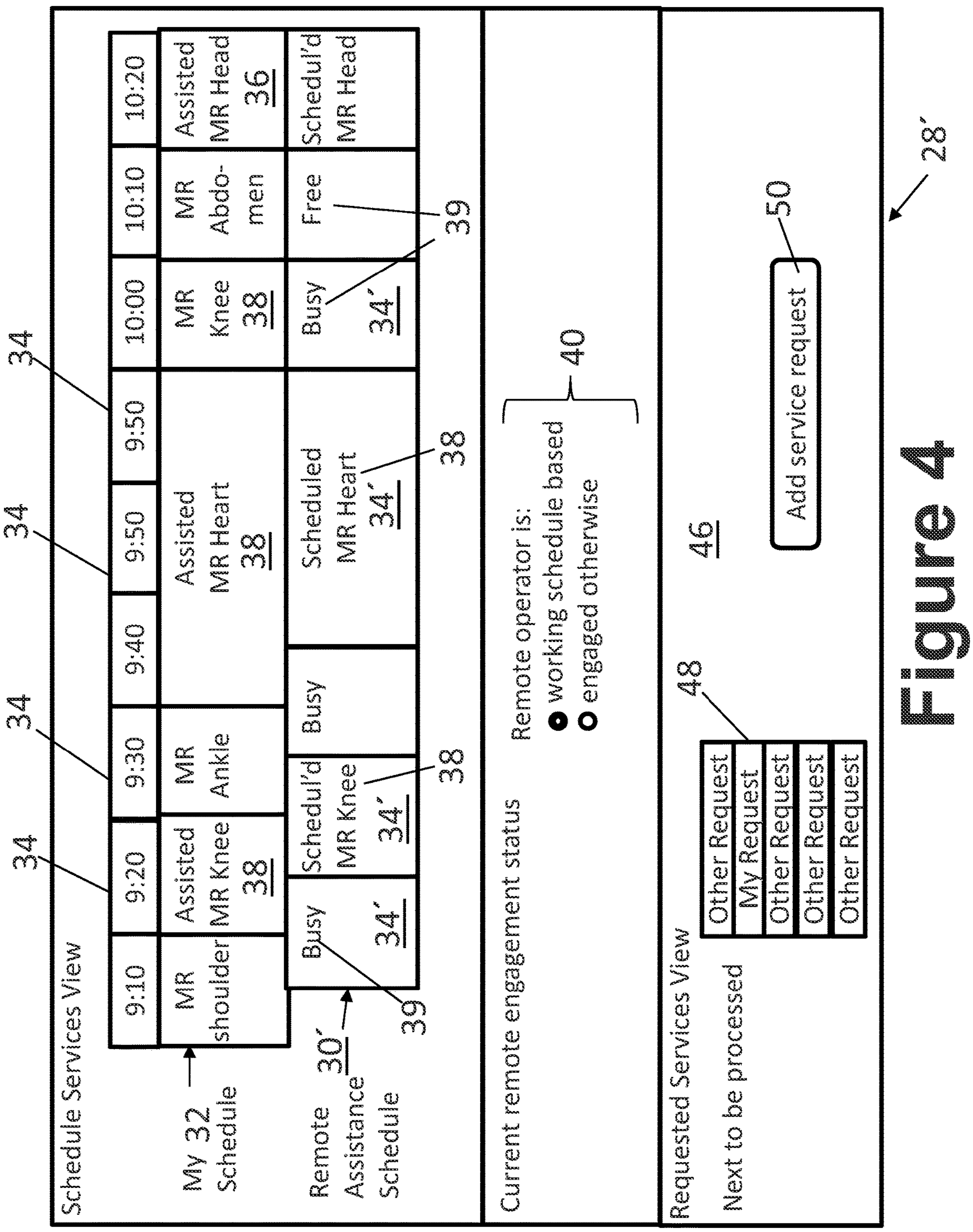

With continuing references to FIGS. 1-3, and now with reference to FIG. 4, at an operation 128, the at least one electronic processor 20 is programmed to control the display device 24' of the medical imaging device controller 10 disposed in the medical imaging device bay 3 to display a timeline 30' with time slots 34' representing availability of the remote operator RO. Alternatively, the timeline 30' may be displayed on some other display located in the medical imaging device bay 3, such as a display of a cellphone carried by the local operator LO (e.g., via an application program or "app" running on the cellphone). This is done by way of the RO availability extractor 112 processing the RO schedule 108 to extract availability information while excluding any information that might impact patient privacy or client confidentiality, and by the schedules view creator 110 which renders this information as the timeline 30'. The processing involved in operation 128 may be variously distributed. The illustrative arrangement in which the RO availability extractor 112 is implemented at (or under control of) the remote service center 4 has an advantage in that it ensures the remote service center 4 has control over the extent to which informational content of the RO schedule 108 is pushed to clients such as the local operator LO. Similarly, implementing the schedules view creator 110 at the local operator end allows for the rendering and display of the timeline 30' to be well-integrated into the overall GUI 28'.

Again, although FIG. 1 only shows a single medical imaging device bay 3, the apparatus can be used in conjunction with a plurality of medical bays located at a plurality of different medical facilities. The apparatus provides assistance by the remote operator RO to a plurality of local operators LO including said local operator shown in FIG. 1. Each local operator LO is a local operator of a respective medical imaging device 2 disposed in a respective medical imaging device bay 3. The operation 128 includes controlling display devices 24' at each respective medical imaging device bay 3 to display the generated timeline 30 on each respective display device. The generated timeline 30 is implemented on a GUI 28' at each respective display device 24'. In some examples, the display device 24' can be an imaging device controller display, a display of the workstation 12', a separate display device, and so forth. The RO availability extractor 112 provides availability information that is specific for each serviced medical imaging device bay 3. The provided availability information includes the more detailed content for those time slots 34 in which the remote operator RO is servicing the medical imaging device bay 3.

In some embodiments, the engagement status 36 of the generated timeline 30 can be altered on each respective display device 24' by the schedules view creator 110 so that display device at each medical imaging device bay 3 displays a timeline 30' tailored to each specific medical bay. The display device 24' at each respective medical imaging device bay 3 can include textual information 38 related only to those work orders of the respective medical facility of which the respective medical imaging bay is a part. This information can be extracted from the LO schedule 104 for the medical imaging device bay 3. For example, as shown in FIG. 4, the timeline 30' representing availability of the remote operator RO is displayed on the display device 24', along with a schedule 32 of work orders to be completed for the local operator LO. The availability timeline 30' of the remote operator RO and the schedule 32 of the local operator LO are displayed so that the work corresponding time slots 34, 34' are vertically aligned. The local operator schedule 32 shows detailed textual information 38 (e.g., work order imaging type and patient region to be imaged) extracted from the LO schedule 104.

However, the remote operator availability timeline 30', as displayed on the local operator display device 24', shows detailed textual information 38 about work orders to be performed at the respective medical bay 13 where the local operator LO is located, but only shows limited information 39 (e.g., "Busy" or "Free") for time slots in which the remote operator is not engaged in assisting work orders to be performed at the respective medical bay 13 where the local operator LO is located. The limited information 39 for time slots 34' is due to the RO availability extractor 112 not providing more detailed information on these time slots. The RO availability extractor 112 provides availability information that is specific for each serviced medical imaging device bay 3, so that the provided availability information includes the additional content 38 shown in the time slots 34'.

Hence, in some embodiments, the textual information 39 in the work orders that are not being performed at the respective or corresponding medical imaging device bay 3 can be shown as a textual message indicating the remote operator RO is busy without identifying the work orders. For example, as shown in FIG. 4, only the time slots 34' with work orders to be performed at that particular medical imaging device bay 3 are shown with detailed textual information. Specifically, looking at the remote operator timeline 30 as shown in FIG. 3 and the remote operator timeline shown in FIG. 4, only the textual information 38 for the "Site 1" work orders are shown. In addition, the textual information 39 for work orders at other medical bays 3 (e.g., Site 2, Site 3, etc.) are set to a message says "busy", as shown in FIG. 4.

In other embodiments, the color, shading, and/or hatching of each time slot 34' that is performed at a different medical imaging device bay 3 than the corresponding medical bay at which at least one of the local operators LO is located. For example, as shown in FIG. 4, the time slots 34' corresponding to the work orders for the medical imaging device bay 3 can be color coded with a first color (e.g., green), and the other time slots 34' for work orders at other sites can be color coded with a second different color (e.g., red). In another example, the time slots 34' can be color coded (or shaded, or hatched) according to the respective medical imaging device bay 3 (e.g., the time slots for Site 1 can be colored green, the time slots for Site 2 can be colored blue, the time slots for Site 3 can be colored red, and so forth). Advantageously, the setting of the textual information 38 and/or the changing of the color/shade/hatching of the time slots 34' for different medical bays 3 prevents the improper obtaining of knowledge of work orders at other medical bays by a local operator LO at the respective medical bay.

In other embodiments, the local operator LO can view the progression of the RO schedule 108 via the remote operator availability timeline 30' throughout the day. In one example, the remote operator RO can provide an input, via the at least one user input device 22, an indication that one or more of the work orders shown in one of the time slots 34 has been completed, rescheduled for a different time, and so forth. Once such an input is received, the timeline 30 shown on the remote operator display device 24 and the RO timeline 30' shown on the local operator display devices 24' are updated accordingly. In another example, the remote operator RO can provide an input, via the at least one user input device 22, an indication of the engagement status 36 in the user dialog 40 (e.g., whether the remote operator is working according to the RO schedule 108, otherwise engaged, and so forth). Once this input is received, user dialogs 40' of the timelines 30, 30' shown at the local operator (s) display device (s) 24' are updated accordingly.

In an operation 130, the at least one electronic processor 20 of the remote operator workstation 12 is programmed to receive at least one request 48 from one or more of the local operators LO. The request 48 can include a requested time needed for assistance (e.g., "I need help in ten minutes"), assistance with a type of modality (e.g., "I need help after contrast agent administration"), assistance with pre-imaging/post-imaging procedures, and so forth. The timeline 30 on the remote operator display device 24 and each of the local operator display devices 24' can be updated based on the requests(s) 48. As shown in FIGS. 3 and 4, the requests 48 can be displayed as a list in the requested services view field 46 on the remote operator display device 24 and each of the local operator display devices 24'. In one example, the requested services field view 46 as displayed on the local operator display devices 24' can be color-coded/shaded/hatched according to the local operator LO who made the request, so that the local operator at the corresponding medical imaging device bay 3 can see where their request 48 is in the list. As shown in FIG. 4, the timeline 30' displayed on the local operator display device 24' can include a button 50 for selection by the local operator LO to add a request 48.

In an operation 132, the timelines 30, 30' as displayed on the remote operator display device 24 and each of the local operator display devices 24' are updated with the request if the requested time is available (e.g., in a free time slot 34). In another example, if the requested time is not available, the remote operator RO can send a message via the workstation 12 to the workstation 12' of the local operator LO who made the request 48 that the requested time is not available. The local operator LO can then make a new request 48 with a new requested time, send a message to the remote operator RO asking for an available time, and so forth. In another example, the request 48 can include a request for a specific remote operator RO. Again, the timeline 30 can be updated if the requested remote operator RO is available, or a message can be sent to the requesting local operator LO if the requested remote operator is not available. The local operator LO can again send a message asking when the requested remote operator RO is available.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for providing assistance by a remote operator to a local operator of a medical imaging device disposed in a medical imaging device bay via a communication link from a remote service center to the medical imaging device bay, the apparatus comprising:
- a workstation disposed in the remote service center including at least one workstation display; and
- at least one electronic processor programmed to:
  - mirror a display of an imaging device controller of the medical imaging device at the at least one workstation display by receiving a screen mirroring data stream sent to the workstation from the imaging device controller and presenting the screen mirroring data stream at the workstation as a shared screen of the imaging device controller generated from the screen mirroring data stream, wherein the mirrored display of the imaging device controller includes at least one configuration display for adjusting configuration settings of the medical imaging device;
  - present video, on the at least one workstation display, of the medical imaging device acquired by a camera disposed in the medical imaging device bay;
  - generate a timeline of a schedule of the remote operator, wherein the generated timeline is tailored to the medical imaging device bay operated by the local operator and determined based on a real-time state of a schedule of the local operation, wherein the generated timeline includes a plurality of time slots and time slot information, including an engagement status of the remote operator, for each time slot, wherein the mirroring of the display of the imaging device controller is performed based on the generated timeline of the schedule of the remote operator;
  - for each time slot of the plurality of time slots, determine whether the remote operator is scheduled to assist the local operator of the medical imaging device at the time slot;
  - for each time slot that the remote operator is not scheduled to assist the local operator, determine, in the time slot information, privacy data of a patient to be serviced by the remote operator at the time slot, and generate the time slot information to exclude the privacy data of the patient; and
  - control a display device in the medical imaging device bay to display the generated timeline to the local user.

2. The apparatus according to claim 1, wherein the control of the display device in the medical imaging bay to display the generated timeline includes:
- coding the time slots by at least one of color coding, shading, or hatching to indicate whether the engagement status for each time slot is busy or available.

3. The apparatus according to claim 1, wherein the at least one electronic processor is programmed to:
- receive, via a user dialog presented on the at least one workstation display, a current engagement status of the remote operator; and
- control the display device in the medical imaging device bay to display the received current engagement status of the remote operator.

4. The apparatus according to claim 1, wherein the apparatus provides assistance by the remote operator to a plurality of local operators including said local operator, each local operator being a local operator of a respective medical imaging device disposed in a respective medical imaging device bay, and the control of the display device in the medical imaging device bay to display the generated timeline includes controlling display devices in the respective medical imaging device bays to display the generated timeline on each respective display device.

5. The apparatus according to claim 4, wherein the engagement status of the remote operator for the time slots includes textual information related to work orders for which the remote operator is to assist in respective time slots, and the at least one electronic processor is programmed to:

display the generated timeline on the display device of each respective medical imaging device bay including only the textual information related to those work orders of a medical facility of which the respective medical imaging device bay is a part.

6. The apparatus according to claim 5, where the display of the generated timeline on the display device of each respective medical imaging device bay includes:

modifying at least one of a color coding, a shading, or a cross-hatching of each time slot that is performed at a different medical imaging device bay than the corresponding medical imaging device bay at which at least one of the local operators is located.

7. The apparatus according to claim 5, where the display of the generated timeline on the display device of each respective medical imaging device bay includes:

changing textual information in the work orders not being performed at the corresponding medical imaging device bay to a textual message indicating the remote operator is busy without identifying the work orders.

8. The apparatus according to claim 4, wherein the at least one electronic processor is programmed to:

receive a user input from the remote operator indicating that one of the work orders in a corresponding time slot is completed or delayed to a later time slot; and modify the timeline based on the received user input.

9. The apparatus according to claim 8, wherein the at least one electronic processor is programmed to:

modify the timeline at the medical imaging device bay of the local operators based on the user input provided by the remote operator.

10. The apparatus according to claim 1, wherein the at least one electronic processor is programmed to:

receive at least one request from the local operator indicating a need for assistance at a requested time;

update the timeline based on the requested time of the at least one request.

11. The apparatus according to claim 10, wherein the at least one electronic processor is programmed to:

update the timeline with the at least one request at the time slot corresponding to the requested time; and generate and transmit a message to the local operator who made the request that the requested time is not available when the requested time is not available.

12. The apparatus according to claim 10, wherein the at least one electronic processor is programmed to:

receive at least one request from a local operator indicting a need for assistance at a requested time and for a specific remote operator;

generate and transmit a message to the local operator who made the request when the requested remote operator is not available.

13. The apparatus according to claim 10, wherein the at least one electronic processor is programmed to:

generate a user dialog on the timeline listing the received at least one request.

14. A non-transitory computer readable medium storing instructions for providing assistance by a remote operator to a local operator of a medical imaging device disposed in a medical imaging device bay via a communication link from a remote service center to the medical imaging device bay, the instructions, when executed by a processor, cause the processor to:

present information pertaining to control of the medical imaging device on a display of an imaging device controller of the medical imaging device;

mirror the display of the imaging device controller of the medical imaging device at a workstation disposed in the remote service center, wherein the workstation includes at least one workstation display, and wherein the mirrored display of the imaging device controller includes at least one configuration display for adjusting configuration settings of the medical imaging device;

present, on the at least one workstation display, video of the medical imaging device acquired by a camera disposed in the medical imaging device bay;

generate a timeline of a schedule of the remote operator, wherein the generated timeline is tailored to the medical imaging device bay operated by the local operator and determined based on a real-time state of a schedule of the local operation, wherein the generated timeline includes a plurality of time slots and time slot information, including an engagement status of the remote operator, for each time slot, wherein the mirroring of the display of the imaging device controller is performed based on the generated timeline of the schedule of the remote operator;

for each time slot of the plurality of time slots, determine whether the remote operator is scheduled to assist the local operator of the medical imaging device at the time slot;

for each time slot that the remote operator is not scheduled to assist the local operator, determine, in the time slot information, privacy data of a patient to be serviced by the remote operator at the time slot, and generate the time slot information to exclude the privacy data of the patient; and control a display device in the medical imaging device bay to display the generated timeline;

wherein the controlling of the display device in the medical imaging device bay to display the generated timeline includes controlling display devices in the respective medical imaging device bays to display the generated timeline on each respective display device.

15. The non-transitory computer readable medium according to claim 14, wherein the engagement status of the remote operator for the time slots includes textual information related to work orders for which the remote operator is to assist in respective time slots, and the controlling of the display device further includes:

displaying the generated timeline on the display device of each respective medical imaging device bay including only the textual information related to those work orders of a medical facility of which the respective medical imaging device bay is a part.

16. The non-transitory computer readable medium according to claim 15, wherein the instructions, when executed by the processor, further cause the processor to:

modify a color or a cross-hatching of each time slot that is performed at a different medical imaging device bay than the corresponding medical imaging device bay at which at least one of the local operators is located.

17. The non-transitory computer readable medium according to claim 15, wherein the instructions, when executed by the processor, further cause the processor to:

change textual information in the work orders not being performed at the corresponding medical imaging device bay to a textual message indicating the remote operator is busy without identifying the work orders.

18. A method of providing assistance by a remote operator to a local operator of a medical imaging device disposed in a medical imaging device bay via a communication link from a remote service center to the medical imaging device bay, the method comprising:

mirroring a display of an imaging device controller of the medical imaging device at a workstation disposed in the remote service center including at least one workstation display to match the display of the imaging device controller, wherein the mirrored display of the imaging device controller includes at least one configuration display for adjusting configuration settings of the medical imaging device;

presenting, on the at least one workstation display, video of the medical imaging device acquired by a camera disposed in the medical imaging device bay;

generating a timeline of a schedule of the remote operator, wherein the generated timeline is tailored to the medical imaging device bay operated by the local operator and determined based on a real-time state of a schedule of the local operation, wherein the generated timeline includes a plurality of time slots and time slot information, including an engagement status of the remote operator, for each time slot, wherein the mirroring of the display of the imaging device controller is performed based on the generated timeline of the schedule of the remote operator;

for each time slot of the plurality of time slots, determining whether the remote operator is scheduled to assist the local operator of the medical imaging device at the time slot;

for each time slot that the remote operator is not scheduled to assist the local operator, determining, in the time slot information, privacy data of a patient to be serviced by the remote operator at the time slot, and generating the time slot information to exclude the privacy data of the patient; and at a display device in the medical imaging bay, displaying to display the generated timeline;

receiving at least one request from a local operator at the medical imaging device bay, the at least one request indicating a need for assistance at a requested time, wherein the at least one request from the local operator is a request for assistance in performing injection of a contrast agent, or a request for assistance after a contrast agent is injected; and updating the timeline based on the requested time of the at least one request.

19. The method according to claim 18, further comprising:

updating the timeline with the at least one request at the time slot corresponding to the requested time; and generating and transmitting a message to the local operator who made the request that the requested time is not available when the requested time is not available.

20. The method according to claim 18, wherein the at least one request from the local operator is a request for assistance in performing injection of a contrast agent.

* * * * *